US007262281B2

(12) United States Patent
Sleytr et al.

(10) Patent No.: US 7,262,281 B2
(45) Date of Patent: Aug. 28, 2007

(54) METHOD OF DEPOSITING S-LAYER PROTEINS ON A CARRIER TO IMMOBILIZE FUNCTIONAL MOLECULES

(75) Inventors: Uwe B. Sleytr, Vienna (AT); Margit Sara, Ganserndorf (AT); Wolfgang Kautek, Vienna (AT)

(73) Assignee: NANO-S Biotechnologie GmbH, Vienna (AT)

( * ) Notice: Subject to any disclaimer, the term of this patent is extended or adjusted under 35 U.S.C. 154(b) by 417 days.

(21) Appl. No.: 10/722,962

(22) Filed: Nov. 26, 2003

(65) Prior Publication Data

US 2004/0137527 A1    Jul. 15, 2004

(30) Foreign Application Priority Data

May 29, 2001  (AT) ............................... A 843/2001
May 29, 2002  (AT) ..................... PCT/AT02/00165

(51) Int. Cl.
*C07K 1/04*       (2006.01)
*C07K 17/00*      (2006.01)
*C07K 17/02*      (2006.01)
*C12N 11/00*      (2006.01)
*C12N 11/02*      (2006.01)
*G01N 33/543*     (2006.01)
*G01N 33/544*     (2006.01)

(52) U.S. Cl. .................... 530/402; 435/174; 435/177; 436/518; 436/528; 530/810; 530/812

(58) Field of Classification Search .................... None
See application file for complete search history.

(56) References Cited

U.S. PATENT DOCUMENTS

| 4,752,395 A | 6/1988 | Sleytr et al. ............... 210/490 |
| 4,886,604 A | 12/1989 | Margit et al. ............... 210/653 |
| 6,296,700 B1 * | 10/2001 | Sleytr et al. ................... 117/84 |

FOREIGN PATENT DOCUMENTS

| EP | 189019 A | 7/1986 |
| EP | 463859 A2 | 1/1992 |
| WO | WO 01/81425 A1 | 11/2001 |

OTHER PUBLICATIONS

International Search Report mailed Sep. 23, 2002.

Sleytr, E. B. et al., "Crystalline Bacterial Cell Surface Layers (S-Layers): A Versatile Self-Assembly System" Chapter 5 from "Supramolecular Polymers", ed. A Ciferri, Marcel Dekker Inc., New York 2000 (ISBN 0-8247-0252-2).

Neubauer, A. et al., "Pulsed-Laser Metal Contacting of Biosensors on the Basis of Crystalline Enzyme-Protein Layer Composites", Sensors and Actuators B40, 1997, pp. 231-236.

Pum, D. et al., "Physico-Chemical Properties of Crystalline Nanoscale Enzyme-Protein-Metal Layer Composites in Biosensors", Ber. Buntenges. Phys. Chem. 101, 1997, pp. 1686-1689.

Neubauer, A. et al., Electrochemical Deposition Through and Electron Beam Deposition on S-Layer Templates: a Step Towards Calibration Standards in the 10-nm Range PTB Reports P-34, 1998, pp. 75-81.

Sleytr, E. B. et al., "Two-Dimensional Protein Crystals (S-Layers): Fundamentals and Applications", Journal of Cellular Biochemistry, Bd. 561 Nr. 2, 1994, pp. 171-176.

D. Pum et al, "The Application of Bacterial S-Layers in Molecular Nanotechnology", Trends in Biotechnology, Elsevier, Amsterdam, NL, Bd. 17, Nr. Jan. 1, 1999, pp. 8-12.

Jap, BK et al., "2D Crystallization: From Art to Science", Ultramicroscopy, Amsterdam, NL, Bd. 46, 1992, pp. 45-84.

Kuepcue, S. et al., "The Crystalline Cell Surface Layer From Thermoanaerobacter Thermohydrosulfuricus L111-69 As An Immobilization Matrix: Influence of the Morphological Properties and the Pore Size of the Matrix on the Loss of Activity of Covalently Bound Enzymes", Biotechnology and Applied Biochemistry, Academic press, U>, Bd. 21, Nr. Part 3, Jun. 1, 1995, pp. 275-286.

Sleytr, U. B. et al., "Application Potential of 2D Protein Crystals (S-Layers)", Annals of the New York Academy of Sciences, US, Nov. 30, 1994, Bd. 745, pp. 261-269.

* cited by examiner

*Primary Examiner*—David M. Naff
(74) *Attorney, Agent, or Firm*—Anton P. Ness; Fox Rothschild LLP (57) ABSTRACT

On a carrier surface, a layer of S-layer proteins is produced as a carrier of functional molecules. A solution containing S-layer proteins in the form of monomers or oligomers is brought into contact with the carrier surface. Electrochemical conditions are produced in the solution such that the S-layer proteins (SU) have an electrical net charge by establishing an electrochemical potential difference between the solution and the carrier surface such that the S-layer proteins accumulate on the carrier surface. A two-dimensional crystalline structure is formed in the layer, and this can occur at a time separate from the deposition of the S-layer proteins, and under different electrochemical conditions.

15 Claims, 3 Drawing Sheets

METHOD OF DEPOSITING S-LAYER PROTEINS ON A CARRIER TO IMMOBILIZE FUNCTIONAL MOLECULES

CROSS-REFERENCE TO RELATED APPLICATIONS

This application claims the benefit of Austrian Patent Application Serial No. A 843/2001, filed 29 May 2001 and PCT Patent Application Serial No. PCT/AT02/00165, filed 29 May 2002.

FIELD OF THE INVENTION

The present invention relates to a method for producing a layer of functional molecules on a carrier surface using cell surface layer proteins (S-layer proteins) as a carrier of the functional molecules in which an S-layer protein in the form of a solution containing monomers or oligomers is brought into contact with the carrier surface, a layer of S-layer proteins is deposited on the carrier surface, and a two-dimensional crystalline structure is configured in the layer thus formed.

BACKGROUND OF THE INVENTION

The production of recrystallized S-layers from crystalline cell surface layers containing proteins (bacterial cell surface layers) on solid or liquid substrates is described, for example, in European Patent 0 154 620 B1 (=U.S. Pat. No. 4,752,395), which specifically relates to the production of multi-layer S-layers of prokaryotes and their use as ultrafiltration membranes.

S-layers are comprised of proteins that occur in prokaryotes as cell wall components, the amino acid sequence of an S-layer protein being generally type-specific or strain-specific; the S-layer proteins are usually simple proteins or glycoproteins. Currently, several hundred bacteria strains are known whose cell surfaces have crystalline structures. The lattice constants of these structures are within the range of approximately 3 to 35 nm, and the S-layers as monomolecular layers for the most part are 3 to 30 nm thick.

Isolated—split off from the original cell—S-layer proteins show the capability of assembling from a solution monomolecular crystal lattices (S-layers), which generally correspond to the crystal structures in the cell wall of an intact cell. Generally, a complete disintegration of S-layers in concentrated solutions of chaotropic agents is achievable by either lowering or raising the pH value. In the reconstitution of the S-layer proteins ("recrystallization"), flat layers, tubular structures such as cylinders and enclosed structures (vesicles) can form—so-called self-assembly products—and specifically as a function of the intrinsic properties of the S-layer proteins and the conditions in the S-layer formation, such as pH value, ion strength and ion composition of the solution; multi-layer S-layers can also form in addition to mono-layers. The formation of the S-layers occurs by self-assembly, because all information for the formation of the S-layer structure is contained in the individual monomers. The S-layers preferably form on boundary layers, for example, on the air/water boundary, on lipid films or on a solid substrate surface such as that of a silicon wafer, an electrode or a synthetic polymer. Due to the specific surface properties of the S-layer protein units, such as charge distribution, hydrophobia, specific interaction with components of the boundary layer, a defined orientation of the S-layer units (monomers, oligomers or small crystallites) occurs in the addition to the boundary layer and incorporation into the S-layer lattice.

S-layers represent highly porous membranes, wherein the pores as a part of the S-layer lattice have a uniform size and shape within the range of approximately 2-6 nm; the porosity can constitute up to 70% of the area. Using S-layer lattices for the immobilization of different molecules, because of the great thickness and defined position and orientation of functional groups that are arranged on the surface of the S-layer units, is known. In order to produce covalent bonds between the S-layer subunits and improve the stability characteristics, S-layer lattices were cross-linked with homobifunctional, amino-group-specific cross-linking agents of various lengths (for example, glutaraldehyde). Many enzymes that were immobilized on activated terminal groups of the S-layer proteins formed a monolayer of tightly arranged molecules on the outer surface of the S-layer lattice. The very specific morphological and biophysical characteristics of S-layer proteins, especially their capability of organizing themselves into monomolecular crystalline lattices that have on their surface a spatially defined arrangement of functional groups and pores of equal sizes and morphology, have led to a broad spectrum of applications in biotechnology, nanotechnology and biometrics.

For further details on S-layers, refer to the article, "Crystalline Bacterial Cell Surface Layers (S-Layers): A Versatile Self-assembly System" by U. B. Sleytr et al., Chapter 5 from "Supramolecular Polymers", ed. A Ciferri, Marcel Dekker Inc., New York 2000 (ISBN 0-8247-0252-2).

A use of S-layers for the production of sensor systems is described by A. Neubauer et al. in Sensors and Actuators B 40 (1997) 231-236. This article deals with deposition of a gold layer on an S-layer by means of the so-called PLD method ("pulse laser deposition", Deposition Using a Pulsed Laser under a High Vacuum Conditions), enzymes such as glucose oxidase having been immobilized on the S-layer beforehand. Additional methods for the deposition of metal layers on S-layers are addressed by, among others, D. Pum et al. in Ber. Bunsenges. Phys. Chem. 101 (1997) 1686-1689 and A. Neubauer et al. in PTB reports P-34 (1998), pp. 75-81. The latter article also discusses the electrochemical deposition of a metal layer (e.g. gold) on an S-layer but with less satisfactory success, because the deposited metal layer has a granular structure that does not correspond to the structure of the S-layer situated beneath it.

In the deposition of an S-layer from a solution that contains S-layer proteins, the S-layer units are deposited directly onto the substrate surface. They are first present unorganized on the surface; the formation of the crystalline structure occurs first in the course of the deposition process, starting in the usual way from crystallization nuclei. Especially if the density of the S-layer proteins on the substrate surface is not yet very large, the individual units can move around on the surface, the mobility being a function of, among other things, the type of the surface. The transition into an ordered structure frequently occurs spontaneously, if S-layer units are deposited in sufficient quantity on the substrate surface. Even after the formation of a crystalline S-layer, dissolved S-layer proteins can precipitate from the solution and attach to the S-layer lattice.

Already in known deposition methods, S-layer units in the solution assemble into S-layers and S-layer self-assembly products of undefined size that remain in solution or suspension or deposit onto the substrate. This operation thus enters into competition with the direct deposition of S-layer units onto the substrate. As a result, controlling the production process of an S-layer turns out to be difficult—especially if a mono layer is to be reliably deposited. Furthermore, the process of S-layer-unit deposition can result in the formation of crystalline double and multiple layers. This process is very disruptive for many applications, because the second (exposed) S-layer is for the most part bonded as a mirror image to the first S-layer (bonded to the substrate surface) and thus masks its functional S-layer domains that are needed for the application.

Moreover, the known methods are in need of improvement with regard to the long-trajectory ordering of the produced S-layer structures. Especially in the crystalline structures that are produced via the aforementioned method, the S-layer structures inevitably contain multiple domains whose expansion is thus rather small. In order to obtain domains of large area, it is desirable to limit the number of domains or the number of nuclei at which point the formation of the crystal structure of the S-layer starts.

European Patent 463 859 A2 describes the deposition of a biomolecular species (e.g. a protein such as glucose oxidase) on a biosensor electrode. In this context, starting from a solution in which the biomolecular species have the same electrical charge signs, a constant current is applied between the biosensor electrode and a counterelectrode, so that the biomolecules migrate between these electrodes to the biosensor electrode and collect there as a film. This publication is thus based on a galvanostatic method in which no consideration is given to a crystal-like ordering of the deposited biomolecules; moreover, the deposited layers, at approximately 1 μm or more, are relatively thick—unlike the actual S-layers in which one or a few (crytalline) monolayers are produced, each of which is 4 to 15 nm thick.

It is therefore the object of the present invention to be able to control the formation of an S-layer and the formation of the S-layer crystal structure in a manner that is an improvement over the known method.

SUMMARY OF THE INVENTION

This objective is resolved by a method of the type mentioned at the outset in which, for the deposition of the S-layer proteins, electrochemical conditions are set in the solution in which the S-layer proteins have an electrical net charge and, by setting the electrical potential of the substrate, an electro-chemical potential difference between the solution and the carrier surface is produced under whose effect the S-layer proteins accumulate from the solution onto the carrier surface and orient themselves in a specific manner.

According to the invention, the formation of the S-layer on the substrate surface is controlled by electrochemical manipulation of the solution substrate system. Setting the electrical potential occurs in an expedient manner potentiostatically; the current that may flow through the electrode is of secondary significance in this context. By time variation of the electrochemical parameters and/or by setting different conditions in the solution and on the substrate surface by means of electrochemical methods, an improved control of the formation of the S-layer is achieved, and the selection of a desired process path of the S-layer formation is possible, which, for example, makes it clearly easier to produce S-layer monolayers or layers with a desired number or sequence of S-layers. Furthermore, a faster covering of the substrate surface and formation of monomolecular, crystalline S-layers, especially on fixed carriers, and a reliably oriented deposition of the S-layer proteins can be achieved.

Figure 1:
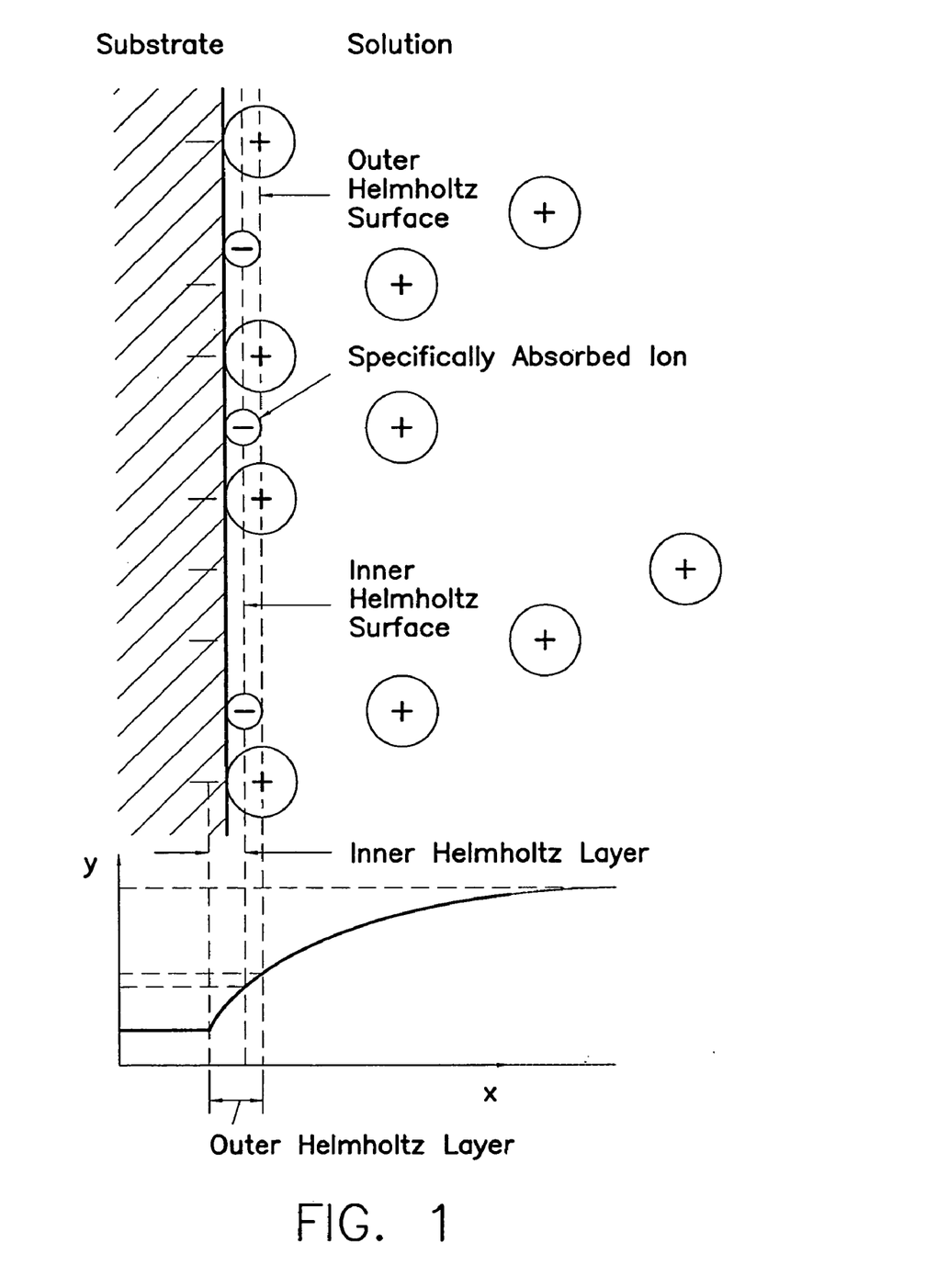
FIG. 1 a diagram of the structure of the electrochemical double layer (according to Gouy, Chapman and Stern)

The electrochemical measures of the present invention succeed in providing a control of the electrostatic charge and the composition of the electrochemical double layer on the substrate surface (so-called Helmholtz layer, FIG. 1) and, to be precise, especially of the extrinsic chemical composition of the outer Helmholtz layer, which is comprised of electrostatically bonded ions, and the inner Helmholtz layer, which is formed by chemically bonded charged particles. Moreover, the invention enables a migration control of the adsorption and desorption by controlling the diffuse portion of the electrochemical double layer, the so-called diffuse layer (above the Helmholtz layer). In these layers, chemical conditions are set directly over the substrate surface that are different from the chemical conditions in the solution and are set for the purposes of depositing and/or crystallizing the S-layer proteins. Therefore, field strengths in the range of $10^5$ V/cm can occur, for example, in the layer directly above the substrate surface. These field strengths represent an important aspect in the addition of the S-layer proteins to the substrate surface from the solution.

Especially noteworthy advantages of the invention are:

(1) Possibility of the improved molecular purification, renewal and reproducible formation of the substrate even before the deposition of the S-layer, because it can also be carried out in situ using electrochemical methods;

(2) Achievability of a high surface area concentration of S-layer subunits (monomers), S-layer oligomers or crystallites (e.g. as nucleation seeds), a concentration excess (surface excess) also being achievable before the formation of the crystal structure;

(3) Improved molecular orientation, e.g. regarding the outside and inside of the S-layer subunits and the nucleation seeds;

(4) Controlled feasibility of a protonization of the S-layer subunits and/or the substrate surface, by means of which the nature of the bond to the substrate surface (fixation) is determinable;

(5) Feasibility of a coadsorption (physical and/or chemical adsorption) of crystallization-promoting substances, e.g. monovalent or bivalent ions, from the solution or from the substrate onto the S-layer;

(6) Feasibility of a coadsorption of reactands, e.g. fixation-promoting;

(7) Feasibility of an electrochemical preservation (i.e. structure stabilization) and/or electrochemical modification of the S-layer sub-units or S-layer crystals or nucleation seeds;

(8) Simplified quality control;

(9) Feasibility of separate methodological steps for the adsorption of S-layer proteins and recrystallization;

(10) Feasibility of continuous processing, wherein the substrate purification, the adsorption of S-layer proteins and the recrystallization can occur in separate steps, physically separated if necessary (e.g. different containers).

Condensed phases of any shape and dimensions, such as plates, porous bodies or dispersed phases (suspensions) are essentially what come into consideration as substrates.

By electrochemical control of the substrate surface, conditions that are optimal for the crystallization of the bonded S-layer subunits can be set for the formation of the crystal lattice. Conditions under which the bonded S-layer subunits can be rearranged in as unhindered a manner as possible, especially by lateral diffusion, into extensive, crystalline S-layer domains are sought in particular. Because S-layer protein lattices for the most part have a different net charge on the outside and inside, the bonding of S-layer proteins to charged surfaces also occurs in a strictly defined orientation. Thus, a directed adsorption of dissolved S-layer proteins (and nucleation seeds, i.e. S-layer crystallites) can be achieved by a controlled setting of the surface charge of a solid carrier. Because the surface charge of S-layer proteins also depends on the pH value of the protein solution, the adsorption operation (orientation of the S-layer proteins in the adsorption) and the strength of the bond of the S-layer proteins to the surface of the solid carrier can also be influenced and optimized by variation of the milieu conditions. A charge-dependent adsorption and crystallization of S-layer proteins can also be used for a specific deposition on structured surfaces (e.g. semi-conductor materials, circuit boards, conductive polymers, composite materials).

The invention also allows the formation of several S-layers on the substrate surface in a defined sequence by corresponding repetition of the particular conditions required for the deposition/crystallization.

In a preferred further development of the invention, the deposition of the S-layer proteins and the formation of the crystalline structure in the deposited protein layer occur separated in time from each other and using different electrochemical conditions of the solution and/or the substrate. In this case, the S-layer subunits are present on the substrate surface in an unorganized state between the deposition and the crystallization and can laterally migrate onto it. The optimal milieu conditions for the adsorption of S-layer monomers/oligomers on the one hand and for the crystallization of the proteins bonded to the surface on the other hand are generally different; they can be set in timed sequence, for example, by continuous changing of the parameters in question.

In this case, the change of the electrochemical conditions can advantageously consist of the electrochemical potential of the carrier surface being changed in relation to the solution between deposition and crystallization. Moreover, to change the electrochemical conditions between deposition and crystallization, at least one chemical parameter of the solution can be varied. The concentrations or ionic strengths of the supporting electrolyte, the pH value, the oxygen concentration or generally the potential for electron transfer reactions as well as the ionic concentration or concentration of dissolved materials in particular come into consideration as chemical parameters. Moreover, the process can also be influenced by the concentration of other ions of the solution or by the temperature. Likewise, to change the electrochemical conditions instead of or in combination with the aforesaid parameters, at least one electrochemical parameter of the substrate, e.g. its charge, the coverage with ions (for example, hydroxyl ions) or chemical modification (morphology of mesoscopic and/or atomic dimension, such as roughness) can also be changed between deposition and crystallization.

The potential of the solution can be measured in an advantageous manner without current by using a reference electrode that is provided in addition to the electrode of the carrier surface and a counter electrode. Expediently, the reference electrode is disposed at a short distance from the surface of that electrode for which primarily the potential difference for the solution is to be determined; the potential difference of the counter electrodes is produced then indirectly through the current regulation of a potentiostat; as a result, actual and setpoint voltage on the electrodes of the carrier surface match each other.

In another advantageous variant of the invention, the electrical net charge of the S-layer proteins is electrostatically impressed on them. For example, by changing the surface charge of the carrier after the protein adsorption, optimal conditions can be set. Moreover, by applying voltages to surfaces, it is also possible to bond or deposit additional charged molecules or metal clusters on the surface of the S-layer lattice or in the pores after the formation of crystalline S-layers.

Moreover, it is beneficial if, during the deposition of the S-layer proteins and/or the formation of crystalline structure, a conformation change of the proteins occurs, especially a denaturing or renaturing. This also facilitates the control of the formation of the S-layer.

The deposition of the S-layer proteins and/or the formation of the crystalline structure can be controlled by a time-varied potential curve, e.g. pulses or ramps.

The protein adsorption and crystallization can also take place in different containers or container compartments under the particular conditions that can be set for the process steps, wherein different solutions that are distinguished, for example, with regard to the dissolved substances while keeping the lead compound and/or of the solvent the same are contained in the containers; this can also occur in a container, for example, by a continuous or discontinuous change of the solution used, such as emptying the first and filling a second solution. Consequently, the deposition of the S-layer proteins on the substrate is carried out in a first solution and the formation of the crystalline structure is carried out in a second solution. In this context it is beneficial if a net charge is electrostatically or electrophoretically impressed on the substrate before dipping in the first solution and is kept when the solutions are changed. In addition, the solutions can be changed by transport of the carrier surface from a first solution bath, in which the deposition occurs, to a second bath for the crystallization (so-called immersion). This corresponds to a batch method. In a variant from this, the transport can occur in a continuous transport process in which, for example, the belt-like or filamentary substrate is routed in succession through different baths in the manner of a conveyor belt, wherein different parts of the same substrate can each be located in a different bath at the same time.

The immobilization of the functional molecules on the S-layer can occur, for example, by the functional molecules being bonded to S-layer proteins even before the deposition of the S-layer proteins and, furthermore, by the functional molecules being deposited at the same time as the deposition of the S-layer proteins. In this context it is expedient if the functional molecules are bonded exclusively or at least in large part on one side of the S-layer proteins—e.g. on that side which corresponds to the inner side of the cell wall— and for the deposition electrochemical conditions are selected under which the S-layer proteins have a resulting dipolar moment, wherein, because of the orientation of the dipolar moment near the carrier surface in the electrical field that exists as a result of the potential difference, said side of the S-layer proteins faces away from the carrier surface.

Alternatively, or in combination with this, the immobilization can occur by functional molecules being deposited on the substrate at positions defined by the crystalline structure after formation of the crystalline structure in the S-layer stratum.

Enzymes, virus proteins or other protein functions, among others, can be used as functional molecules. The functional unit can also be realized by the S-layer proteins having one or more functional units as recombinant fusion protein.

Furthermore, after formation of the crystalline structure in the S-layer stratum, nanoparticles can be deposited or precipitated onto the substrate at positions defined by the crystalline structure. This also includes the use of the S-layer as a template for the deposition of a second phase.

BRIEF DESCRIPTION OF THE DRAWINGS

The present invention is explained in detail below in reference to the attached drawings using several exemplary embodiments, which do not limit the scope of the invention. Shown are.

DETAILED DESCRIPTION OF THE INVENTION

The examples dealt with below describe methodologies in which, according to the invention, a layer of functional molecules are electrochemically precipitated from cell surface layers that contain protein (S-layer proteins) onto an electrically conductive carrier surface using monomers, oligomers or crystallites, brought into two dimensional crystallization and finally electrochemically fixed. A substrate material that can conduct and/or accumulate electrical charges is conditioned in the process in such a manner that (1) adsorption, (2) orientation,

TABLE 1

Theoretical isoelectric points (pI) of the mature S-layer proteins, the N-termini and the remaining sequences. The GBAN line reports the GenBank access number.

| S-layer protein form | SbsB | SbpA | SbsC |
|---|---|---|---|
| GBAN | X98095 | AF 211170 | AF 055578 |
| mature protein | pI 4.95 Amino acid 32-920 | pI 4.60 Amino acid 31-1268 | pI 5.40 Amino acid 31-1099 |
| N-terminus | pI 8.94 Amino acid 32-207 | pI 4.49 Amino acid 31-202 | pI 9.13 Amino acid 31-270 |
| Radical sequence | pI 4.73 Amino acid 208-920 | pI 4.63 Amino acid 203-1268 | pI 4.88 Amino acid 271-1099 |

(3) surface diffusion, (4) crystallization and (5) fixation of S-layer units proceed in an electrochemically controlled process.

Using a potentiostatic electrochemical control of the substrate material, three electrochemical surface types that have the decisive influence on the aforementioned processes can in principle be set. The first range is characterized in that a negative surface charge is present, the second in that a positive net charge is set. The third range, in which even more positive potentials are produced, distinguishes itself in that the surface is electrochemically converted so that henceforth the substrate only continues to interact with adsorbates via a hydroxidic or oxidic surface or via other specific adsorbed ionic species. In the first two ranges, the interaction with adsorbates is predominantly determined by electrostatic forces and only secondarily by chemical forces (e.g. van-der-Waals forces). In the third range, by contrast, chemical (e.g. hydrogen bridge bonds) and non-electrostatic interactions are predominant.

EXAMPLE 1

The layer protein SbsB—e.g. in its recombinantly produced form, which is designated as rSbsBg2-920—as a mature protein has a theoretical isoelectric point (pI) of 4.95. The N-terminal region (amino acids 32-207), which comprises three so-called S-layer homologous motifs (SLH-motifs), has a pI of 8.94; for the remainder of the sequence (amino acids 208-920) a pI of 4.73 was calculated (see Table 1). Experiments with recombinantly produced, N-terminal shortened SbsB shapes, from which up to 3 SLH motifs were missing, confirmed that the N-terminus is not involved in the self-assembly operation.

For the production of soluble S-layer proteins (S-layer monomers or oligomers for the crystallization on solid surfaces) 0.2 mg of S-layer self-assembly products of rSbsB32-920 (monomolecular S-layer-protein crystals with a size of 0.1 to 5 µm) were dissolved in 1 ml of 5 M guanidine hydrochloride (GHCl) in 50 mM TRIS-HCL buffer (pH 7.2), and dialysized for 24 hours at 4° C. using purified water. Because of the low concentration of S-layer protein, the formation of self-assembly products during the dialysis was prevented. Nevertheless, after termination of the dialysis with 40,000 g centrifuged for a period of 20 minutes at 4° C., the clear residue was removed, the pH value of the solution was set with 0.01 N NaOH to 6.5 and 400 µl of this solution was used for the crystallization.

First, a cleaning step was carried out in the electrolytic solution without S-layer protein in which by repeated cycling of the electrode potential between extreme values (e.g. on gold between −1.2 V and +0.8 V against a saturated mercury sulfate electrode) while maintaining the pH value, any contaminate layers were eliminated by the total exchange of the surface atoms of the substrate.

For the subsequent S-layer-adsorption, an electrically conductive material can be used as a solid carrier. In particular, metals such as gold, semiconductors such as silicon, conductive polymers or other materials such as graphite are taken into consideration for this.

The orientation of the adsorbed S-layer subunits can be controlled via the set net charge of the solid carrier. In a first instance, the surface (5 mm$^2$) of the fixed carrier is conditioned in such a manner that it has a negative net charge. Under these conditions, the S-layer subunits bond as a monolayer with the inner side, which includes the N-terminus and at a pH-value of 6.5 is positively charged. In a second case, the surface of the solid carrier is conditioned in such a manner that it has a positive net charge, the S-layer subunits bonding with the outer side, which is negatively charged at a pH value of 6.5.

After adsorption of the S-layer sub units, the S-layer protein solution was removed and washed several times with purified water. In order induce the formation of the crystal lattice, a solution of bivalent cations was added (e.g. 5 mM CaCl$_2$) into purified water and incubated at 20° C. Because the N-terminal portion (pI 8.94) is not involved in the self-assembly process, the neutralization of the negative charges is significant primarily within the range of amino acids 208-920 by the addition of bivalent cations. The verification of a crystalline S-layer structure on the substrate surface was carried out in the AFM scanner microscope ("Atomic Force Microscope"). It was possible to detect monocrystalline ranges having a size of approximately 1-10 µm, but which showed a different orientation in relation to each other.

If, by contrast, for the adsorption the potential is moved into the third range of the oxide formation, the completely changed substrate surface can henceforth accept other vertical chemical bonds (e.g. non-electrostatic interactions) to the already formed crystallized S-layer.

EXAMPLE 2

In these tests, a recombinantly produced rSbsB-streptavidin protein was produced. The functional domain (Streptavidin) is merged on the C-terminal end of the S-layer proteins. The pI of the sequence, which is between amino acids 208-920 of SbsB and includes the heterotetrameric Streptavidin is 5.60. The C-terminal SbsB-Streptavidin-fusion protein is water soluble and forms the diagonal S-layer lattice only on pre-conditioned surfaces (e.g. cell wall sacculi of *Bacillus stearothermophilus* PV72/p2, which contain peptidoglycane of the Alγ-chemo-type and the secondary cell wall polymer that is typical for the organism).

For the recrystallization, a solution that contained 200 µg of the fusion protein in 500 µl purified water was brought into contact with a negatively charged solid surface 5 mm$^2$ in size. The bond of the fusion protein occurred in this case over the positively charged N-terminal region at a pH value of 6.0. For the stabilization of the S-layer lattice, 500 µl of a solution that contained 1-ethyl-3,3'-dimethlylaminopropyl-carbodiimide (EDC) as a zero-length crosslinker (1 mg EDC per ml of purified water, the pH value of the solution being set with 0.01 M HCl to 4.75) were added and incubated for 60 minutes at 20° C. EDC can only cross-link at those places where amino and carboxyl groups are present in direct electrostatic interaction, such as in the case of adjacent S-layer subunits. After the incubation, the carrier was washed several times with purified water. Then the structure of the S-layer lattice was examined in the AFM microscope. The diagonal S-layer lattice could clearly be seen. The differently oriented areas had a size of approximately 1-10 µm.

EXAMPLE 3

The mature S-layer protein SbpA (amino acids 31-1268; pI 4.60; see Table 1) crystallizes in a square lattice. The N-terminal part (amino acids 31-202) of the mature S-layer proteins comprises the 3 SLH motifs and the bonding region for the secondary cell wall polymer and has a pI of 4.49. The pI of the remaining sequence (amino acids 203-1268) is at 4.68. The N-terminal part is not involved in the self-assembly operation.

Bivalent cations are necessary for the formation of self-assembly products with square lattices. A solution that contained 200 µg of rSbpA per ml of purified water and a pH value of 6.0 was applied to a positively charged carrier surface 5 mm$^2$ in size and incubated at 20° C. for 2 hours. Then, the excess S-layer protein solution was washed away. For the formation of the crystal lattice, a 10 mM CaCl$_2$ solution was applied to the carrier surface and incubated for 2 hours at 20° C. After washing with purified water, the carrier was examined in the AFM. Areas approximately 0.5 µm in size with a square lattice could be recognized; the two differently structured areas were present in an approximately 1:1 ratio. It was concluded from this that the S-layer sub units could adsorb with the inner side (rough surface) as well as with the outer side (smooth surface). This example shows that a uniformly oriented deposition of the S-layer subunits only occurs on a charged substrate if S-layer subunits on their inner and outer surface have differently charged domains (see examples 2 and 3).

EXAMPLE 4

The recombinantly produced fusion protein rSbsC-Bet v 1 was to be crystallized on solid surfaces. In the rSbsC-Bet v 1, the sequence of the main birch pollen allergen Bet v 1 (161 amino acids) is merged via 2 glycine radicals as linkers on the C-terminal end of a shortened SbsC-form that includes amino acids 31-920 and has a pI of 6.09. The mature SbsC (amino acids 31-1099) has a pI of 5.40. The pI of the N-terminal region (amino acids 31-270) is at 9.13; that of the radical sequence (amino acid 271-1099) is 4.88 (see Table 1). The N-terminal part is involved in the self-assembly operation.

For the crystallization, a solution of 250 µg rSbsC-Bet v 1 fusion protein per ml of purified water with a pH value of 6.0 was applied to a solid surface with a negative net charge. In this way, the adsorption of the fusion protein occurred via the positively charged N-terminus. The Bet v 1 sequence appended to the C-terminal end therefore remained exposed on the outside. After a two-stage incubation at 20° C., a pH valu of 6.09 was set by adding 0.01 M of HCl so that the negative net charge of the C-terminal S-layer protein were lost and the subunits were "compromised"; that is, because of the loss of the net charge, a reciprocal approach occurred. By this operation the regular lattice structure was formed.

EXAMPLE 5

This example illustrates the continuous layering of a substrate in the form of a belt material with S-layers.

Figure 2:
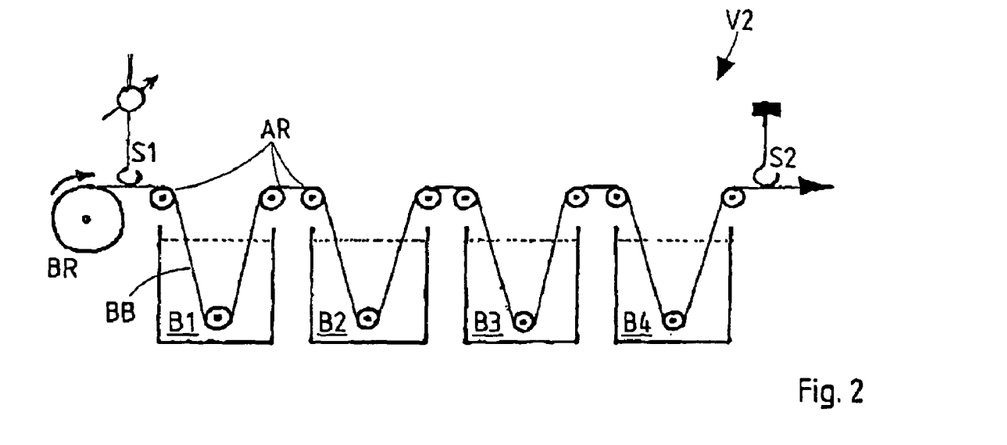
FIG. 2 a device for carrying out a continuous coating process for a belt substrate.

For example, this can occur with a device V2, as shown in FIG. 2. The belt to be coated BB, made of a plastic carrier material, for example, which is metal coated on that side on which the S-layer is to be deposited, is unwound from a roll BR and is guided through containers B1, B2, B3, B4 by appropriate deflection drums or rollers AR. The number of baths in this case is naturally only given as an example and can be adapted to the desired process and increased or reduced accordingly. The conductive belt material is charged in a known manner via sliding contacts S1, S2 or discharged again after the bath sequence (grounding).

In the example considered here, the individual containers are filled as follows:

Container B1: Purified water for washing and purifying the foil;

Container B2: Solution with S-layer protein (rSbsC; 50 µg/ml in purified water at pH 5.7) for loading the foil with S-layer protein;

Container B3: Solution (20 mM CaCl$_2$ solution in purified water) for the crystallization of the adsorbed S-layer proteins;

Container B4: Cross-linking agent solution (0.5% glutaraldehyde in 0.2 M Na-Cacodylate buffer, pH 7.0), in which the chemical cross-linking of the crystalline layer occurs for further stabilization.

The dwell or run time of the belt in each container is between 20 and 120 minutes. After the coating and chemical cross-linking, additional steps (not shown), such as a washing step and a drying step are carried out.

Naturally, instead of bath sequence B1-B4, another bath sequence can also be used, such as corresponds to one of Examples 1 though 4.

Figure 3:
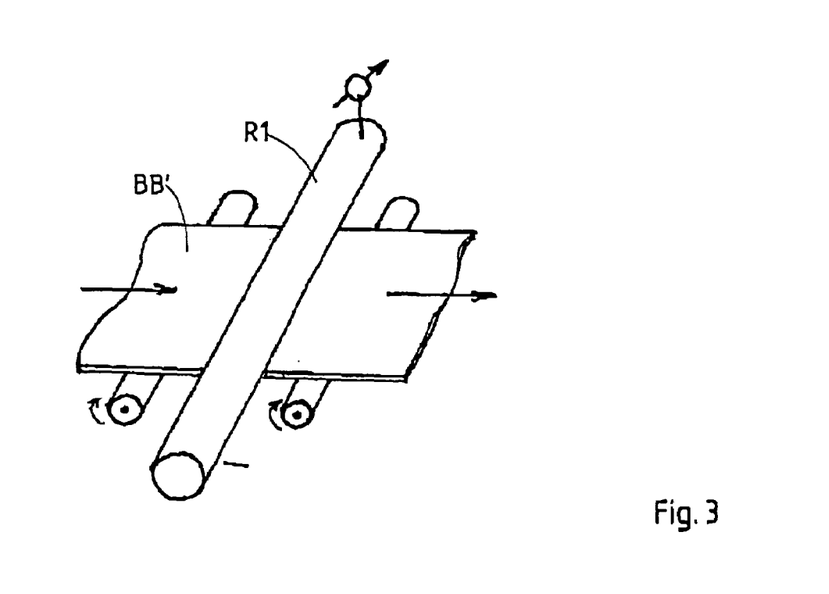
FIG. 3 an arrangement for the electrostatic charging of the belt substrate of FIG. 2.

In a variant from this example, a non-conductive material, such as a polymer film, can be coated. In this case the charging of the belt material does not occur via sliding contacts, as in FIG. 2, but rather electrostatically. In reference to FIG. 3, film BB' is run through in direct contact with or at a slight distance from a charged drum or rod R1 and in this way electrostatically charged. For this purpose rod R1 is expediently set to a high voltage of, for example, 1000 V. This rod R1 would be mounted in device V2 of FIG. 2 instead of sliding contacts S1.

EXAMPLE 6

This example treats the crystallization of an S-layer protein using an electrophoretic method, for example, in an electrochemical suspension cell according to B. Kastenring et al., in J. Electroanal. Chem. 265 (1989), pp. 77-101. In the electrochemical suspension cell described by Kastenring, which is diagrammatically shown in FIG. 4, a rotating part FD made of graphite and of conical shape and structured surface is present on the right side in a first container CC, which is used as a "feed chamber". The rotating part FD is kept at a constant work potential Uw compared to potential U0 of a counterelectrode XC using a potentiometer PS. Furthermore, it is used as a "feed electrode", which is to confer a specific potential to the particles incorporated in the sequence into the cells.

Figure 5A:
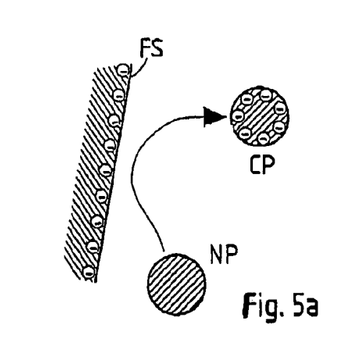
FIG. 5a diagram showing the transmittal of electrical charge to particles NP.
Figure 5B:
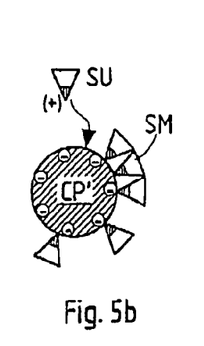
FIG. 5b diagram showing the deposition of S-layer units SU on particle CP.
Figure 5C:
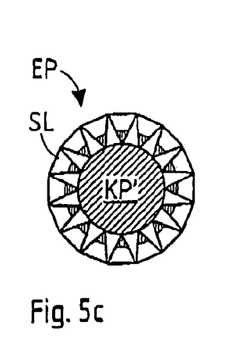
FIG. 5c diagram showing a particle covered by an attached S-layer SL.

The diagrams of FIGS. 5a-5c show the process of S-layer crystallization on the particles. On surface FS of feed electrode FD, electrical charge is transmitted to particles NP, which are located in the suspension and in container CC are run past feed electrode FD—FIG. 5a. In the example considered here, particles CP, which are electrophoretically treated in this way, take on a negative charge from the feed electrode. In the next step—FIG. 5b—the S-layer units SU deposit on particle CP in an orientation that is determined by the distribution of the charged domains and the charge located on the particle surface. In the example considered here, this occurs via the N-terminus of rSbsB, which has a positive net charge and is depicted in FIG. 5c as the shaded tip of the S-layer subunits. On the surface, even the formation of oligomers SM can also take place. By crystallization of the S-layer, one obtains a particle EP that is covered by an attached S-layer SL. Different dispersed materials such as metal particles made of Au, Pt or other metals, carbon in the form of graphite particles or active carbons, plastic-coated particles or magnetic particles can be used as a core KP for these particles.

Figure 4:
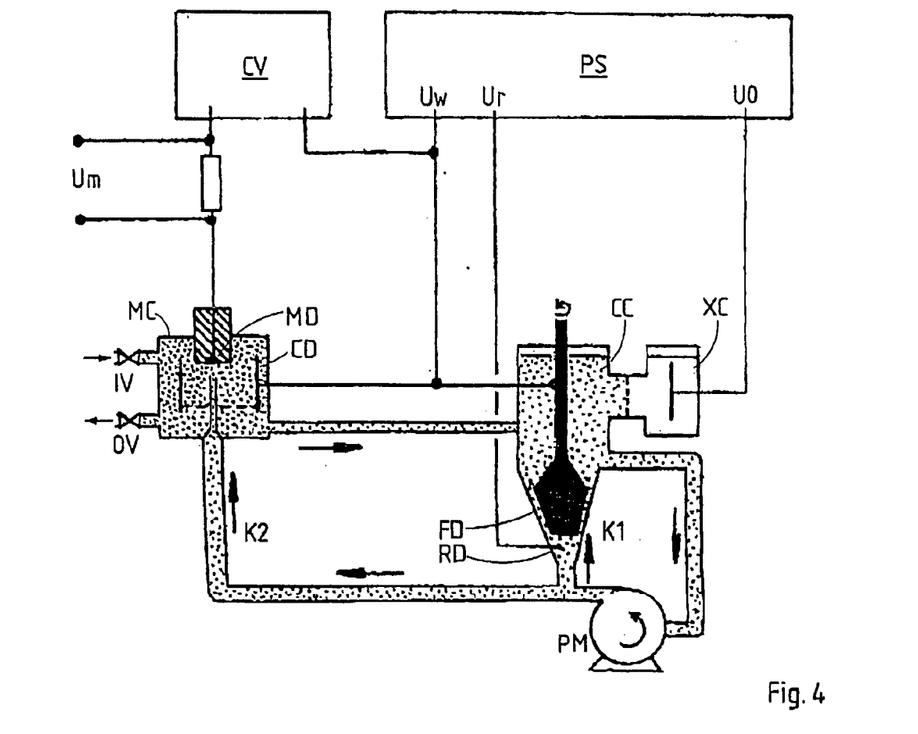
FIG. 4 a device for the potentiostatic S-layer deposition based on an electrochemical suspension cell according to B. Kastening et al.

For the charging of the particles, the solution is run past feed electrode FD in main circulation K1 by means of a pump PM in the apparatus of FIG. 4. Container CC has a reference electrode RD for the current-free measurement of potential Ur of the solution. Moreover, a secondary circulation K2 is provided that leads through a measurement chamber MC in which the charge of the particles suspended in solution can be measured using a measuring electrode MD; for this purpose, for example, a voltage between measuring electrode MD and a cylinder electrode CD at working potential Uw can be developed by means of a constant voltage source CV, and from the current (measured as voltage Um) the charge of the particles can be determined in a known manner. The measurement chamber MC can also be used to feed or carry away the solutions and additives that are used through intake and discharge valves IV, OV.

25 ml of a suspension of 5 g of polystyrene latex balls with a diameter of 1 µm in a buffer solution (0.1 M Na citrate solution, pH 6.0) are poured into the electrochemical suspension cell. Instead of the polystyrene latex balls, polystyrene balls without a latex covering can also be used; both ball materials that are used are products of Banks Lab., in Indiana (USA). The potential of the feed electrode is set in such a manner that the balls take on a negative surface charge, e.g. −1 V compared to the saturated mercury sulfate electrode XC. After a pumping time of 20 minutes, 25 ml of an S-layer protein solution (rSbsB; 0.25 mg per ml of purified water, pH value 6.0) are injected, e.g. in container MC or via branch circuit K2. For the directed adsorption of the S-layer protein via the positively charged N-terminal part situated on the inner side and with a pH value of 6.0, the suspension is circulated for 2 hours at 20° C. This occurs expediently with a circulation in branch circuit K2, circuit K1 being closed by a valve (not shown) in the feed line of container CC; as a result, a deposition of S-layer proteins on the feed electrodes is prevented. Then, the suspension is removed from the cell, centrifuged for 20 minutes at 40,000 grams at 20° C., the clear residual excess is thrown out, and the remaining centrifuge effluent—the so-called pellet—is suspended in 20 ml of a 10 mM $CaCl_2$ solution. The suspension is then lightly stirred for 4 hours at 20° C. In the presence of bivalent cations, the initially adsorbed S-layer protein is rearranged in a connected crystalline S-layer protein lattice. The suspension is then re-centrifuged and washed once with 20 ml of a 10 mM CaCl2 solution. In the pellet that is produced in this way, the functions immobilized on the S-layer (e.g. receptors like antibodies) are available in the form of a suspension in a high concentration.

For the examination in the microscope, 1-2 µl of the pellet were frozen in freon 22 (cooled with liquid nitrogen) and subjected to a freeze etching. For the examination of the formation of the crystalline lattice, the preparation was evaluated in the transmission electron microscope. It was possible to detect a complete coating of the particle with S-layer protein that is assembled in a diagonal lattice.

The invention claimed is:

1. A method for producing a layer of S-layer proteins on a carrier surface to provide a carrier for functional molecules, comprising the steps of:
   providing a carrier surface;
   providing a first solution containing S-layer proteins;
   bringing the first solution into contact with the carrier surface and providing a reference electrode in the first solution;
   depositing the S-layer proteins as a layer on the carrier surface at first electrochemical conditions on the carrier surface while in contact with the first solution, said electrochemical conditions being provided by applying a first electrochemical potential to the carrier surface with respect to said reference electrode in said first solution; and
   forming a two-dimensional crystalline structure in the layer of S-layer proteins while in contact with the first solution or a second solution after being deposited on the carrier surface, at second electrochemical conditions on the carrier surface, said electrochemical conditions being provided by applying a second electrochemical potential to the carrier surface with respect to said reference electrode.

2. The method as described in claim 1, wherein the layer of S-layer proteins is in contact with the first solution when forming the two-dimensional crystalline structure, and between the steps of depositing a layer of S-layer proteins and forming of a crystalline structure, at least one chemical parameter of the first solution is varied.

3. The method as described in claim 1, wherein the layer of S-layer proteins is in contact with the first solution when forming the two-dimensional crystalline structure, and between the steps of depositing a layer of S-layer proteins and forming of a crystalline structure, at least one electrochemical parameter of the first solution is varied.

4. The method as described in claim 1, wherein in at least one of the steps of depositing of the S-layer proteins and forming of a crystalline structure, a conformation change of the S-layer proteins occurs.

5. The method as described in claim 1, wherein at least one of the steps of depositing the S-layer proteins and forming of a crystalline structure is controlled by a time-varied electrochemical potential.

6. The method as described in claim 1, wherein depositing the S-layer proteins is carried out in a first solution containing the reference electrode and forming a crystalline structure is carried out in a second solution.

7. The method as described in claim 6, wherein a net charge is electrostatically applied to the carrier surface before it is brought into contact with the first solution and said net charge is maintained until it is brought into contact with the second solution.

8. The method as described in claim 6, wherein a net charge is electrochemically applied to the carrier surface in the first solution and said net charge is maintained until it is brought into contact with the second solution.

9. The method as described in claim 6, wherein the carrier surface is transported from the first solution for depositing of the S-layer proteins to the second solution for forming the crystalline structure, both the first and second solutions being in contact with the reference electrode.

10. The method as described in claim 1, wherein functional molecules are bonded to S-layer proteins before the depositing of the S-layer proteins, and the functional molecules are deposited on the carrier surface together with the S-layer proteins.

11. The method as described in claim 1, wherein, after formation of the crystalline structure in the layer of S-layer proteins, functional molecules are deposited on the layer at bonding sites of the layer.

12. The method as described in claim 1, wherein, after the formation of the crystalline structure in the layer of S-layer proteins, electrochemical nanoparticles are deposited on the layer at bonding sites of the layer.

13. The method according to claim 1, wherein the electrochemical potential is applied potentiostatically.

14. The method as described in claim 4, wherein the conformation change is denaturing of S-layer proteins.

15. The method as described in claim 4, wherein the conformation change is renaturing of S-layer proteins.

* * * * *